(12) United States Patent
Paul

(10) Patent No.: US 7,070,599 B2
(45) Date of Patent: *Jul. 4, 2006

(54) BONE SUPPORT ASSEMBLY

(76) Inventor: Kamaljit S. Paul, 3220 Old Orchard La., Oshkosh, WI (US) 54901

( * ) Notice: Subject to any disclaimer, the term of this patent is extended or adjusted under 35 U.S.C. 154(b) by 698 days.

This patent is subject to a terminal disclaimer.

(21) Appl. No.: 10/202,705

(22) Filed: Jul. 24, 2002

(65) Prior Publication Data

US 2004/0034354 A1 Feb. 19, 2004

(51) Int. Cl.
*A61B 17/80* (2006.01)
(52) U.S. Cl. .............................. 606/71; 606/61; 606/69
(58) Field of Classification Search ................. 606/61, 606/69, 70, 71
See application file for complete search history.

(56) References Cited

U.S. PATENT DOCUMENTS

| 2,406,832 A | 9/1946 | Hardinge | |
|---|---|---|---|
| 2,486,303 A | 10/1949 | Longfellow | |
| 4,246,660 A | 1/1981 | Wevers | |
| 4,503,848 A | 3/1985 | Caspar et al. | 128/92 |
| 4,513,744 A | 4/1985 | Klaue | |
| 5,324,290 A | 6/1994 | Zdeblick et al. | 606/61 |
| 5,344,421 A | 9/1994 | Crook | 606/61 |
| 5,569,251 A | 10/1996 | Baker et al. | 606/69 |
| 5,578,034 A | 11/1996 | Estes | 606/61 |
| 5,616,142 A | 4/1997 | Yuan et al. | 606/61 |
| 5,616,144 A | 4/1997 | Yapp et al. | 606/61 |
| 5,676,666 A | 10/1997 | Oxland et al. | 606/61 |
| 5,681,311 A | 10/1997 | Foley et al. | 606/61 |
| 5,728,127 A | 3/1998 | Asher et al. | 606/61 |
| 5,876,402 A | 3/1999 | Errico et al. | |
| 5,904,683 A | 5/1999 | Pohndorf et al. | 606/61 |
| 5,951,558 A | 9/1999 | Fiz | 606/70 |
| 5,954,722 A | 9/1999 | Bono | 606/61 |
| 6,017,345 A | 1/2000 | Richelsoph | 606/70 |
| 6,030,389 A | 2/2000 | Wagner et al. | 606/71 |
| 6,106,557 A | 8/2000 | Robioneck et al. | 623/17 |

(Continued)

FOREIGN PATENT DOCUMENTS

DE 28 08 971 9/1979

(Continued)

OTHER PUBLICATIONS

"Blackstone™ Anterior Cervical Plate." Blackstone Medical Inc. Product literature. 4 sheets. No date available.

(Continued)

*Primary Examiner*—David O. Reip
(74) *Attorney, Agent, or Firm*—Wilhelm Law Services, S.C.; Thomas D. Wilhelm

(57) ABSTRACT

Bone support assemblies, methods of fabrication, and methods of use. Such assemblies comprises locking structures assembled to bone support plates. The locking structure comprises elongate bands biased against each other. The bands extend into apertures in the plate. The bands automatically respond to side forces applied by interfering elements of bone fasteners driven through the apertures, by moving away from the interfering elements, and returning to blocking positions over the interfering elements after the interfering elements pass the bands. Methods of fabrication include inserting the locking structure longitudinally into the channel and optionally extending locking studs through the plate and engaging the locking structure. Methods of use include advancing interfering elements of the bone fasteners through the apertures and past the bands. The interfering elements deflect the bands as the interfering elements pass and the bands, return to their initial positions when the interfering elements have moved past the bands.

39 Claims, 6 Drawing Sheets

U.S. PATENT DOCUMENTS

| | | | |
|---|---|---|---|
| 6,129,730 A | 10/2000 | Bono et al. | 606/73 |
| 6,139,550 A | 10/2000 | Michelson | 606/69 |
| 6,152,927 A | 11/2000 | Farris et al. | 606/69 |
| 6,159,213 A | 12/2000 | Rogozinski | 606/70 |
| 6,193,721 B1 | 2/2001 | Michelson | 606/70 |
| 6,224,602 B1 | 5/2001 | Hayes | 606/69 |
| 6,235,034 B1 | 5/2001 | Bray | 606/71 |
| 6,238,396 B1 | 5/2001 | Lombardo | 606/61 |
| 6,241,731 B1 | 6/2001 | Fiz | 606/65 |
| 6,293,949 B1 | 9/2001 | Justis et al. | 606/61 |
| 6,306,139 B1 | 10/2001 | Fuentes | 606/70 |
| 6,364,881 B1 | 4/2002 | Apgar et al. | |
| 6,383,186 B1 | 5/2002 | Michelson | |
| 6,398,783 B1 | 6/2002 | Michelson | |
| 6,402,756 B1 | 6/2002 | Ralph et al. | 606/71 |
| 6,428,542 B1 | 8/2002 | Michelson | |
| 6,454,771 B1 | 9/2002 | Michelson | |
| 6,458,133 B1 | 10/2002 | Lin | 606/69 |
| 6,503,250 B1 | 1/2003 | Paul | |
| 6,533,786 B1 | 3/2003 | Needham et al. | 606/61 |
| 6,602,255 B1 | 8/2003 | Campbell et al. | |
| 6,602,256 B1 | 8/2003 | Hayes | |
| 2002/0151899 A1 | 10/2002 | Bailey et al. | |
| 2003/0018335 A1 | 1/2003 | Michelson | |
| 2003/0045880 A1 | 3/2003 | Michelson | |
| 2003/0083658 A1 | 5/2003 | Hawkes et al. | |

FOREIGN PATENT DOCUMENTS

| | | |
|---|---|---|
| DE | 44 09 833 | 10/1995 |
| EP | 1169971 | 1/2002 |
| FR | 1505513 | 12/1967 |
| FR | 2778088 | 11/1999 |
| WO | WO 00/24325 | 5/2000 |
| WO | WO 00/64359 | 11/2000 |
| WO | WO 01/26566 | 4/2001 |
| WO | WO 01/26567 | 4/2001 |

OTHER PUBLICATIONS

"CSLP Variable Angle: For Use with the Cervical Spine Locking Plate System." Technique Guide. 2000 SYNTHES® Spine. 28 sheets.

Zdeblick, M.D., Thomas A. et al. "Premier™ Anterior Cervical Plate System." Surgical Technique. 2000 Medtronic Sofamor Danek. 30 sheets.

Health Journal, Tara Parker-Pope. The Wall Street Journal, Jan, 2001. 1 sheet.

C-TEK Anterior Cervical Plate, 2001 Interpore Cross International, 1 sheet.

C-TEK Anterior Cervical Plate System, Interpore Cross, Oct. 2000, 1 sheet.

WINDOW Cervical Stabilization System, 2000 Endius, Inc., 10 sheets.

Caspar Instruments for Anterior Cervical Fusion, AESCULAP, undated, 4 sheets.

NDC Internet Data Sheets, date unknown, 3 sheets.

Ni-Ti alloy Internet Data Sheets, date unknown, 4 sheets

U.S. Appl. No. 10/014,409, filed Dec. 14, 2001, Bone Support Assembly, 17 sheets.

U.S. Appl. No. 09/838,646, filed Apr. 19, 2001, Bone Support Assembly, 18 sheets.

"Zenith the perfect alliance for successful cervical funsions," Eurosurgical, Spine A Circuit, date unknown, 2 sheets of internet pages, downloaded Apr. 15, 2003.

"Orla Zenith Product Specifications," REO Spine Line Network, Mar. 2003, 18 sheets.

AESCULAP, Advanced Biomechanical Concept, date unknown, 11 sheets.

"The Market for Spinal Implants," Internet data sheets downloaded May 2001, 4 sheets.

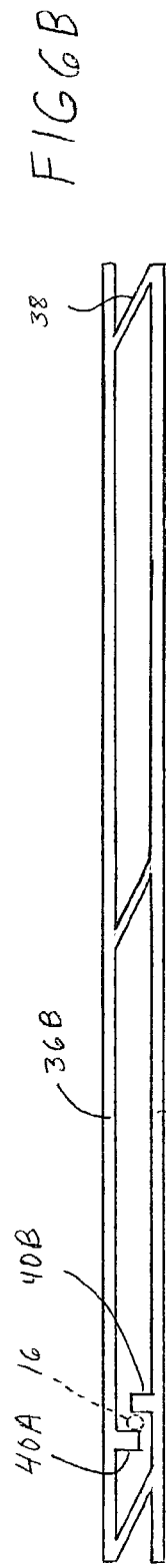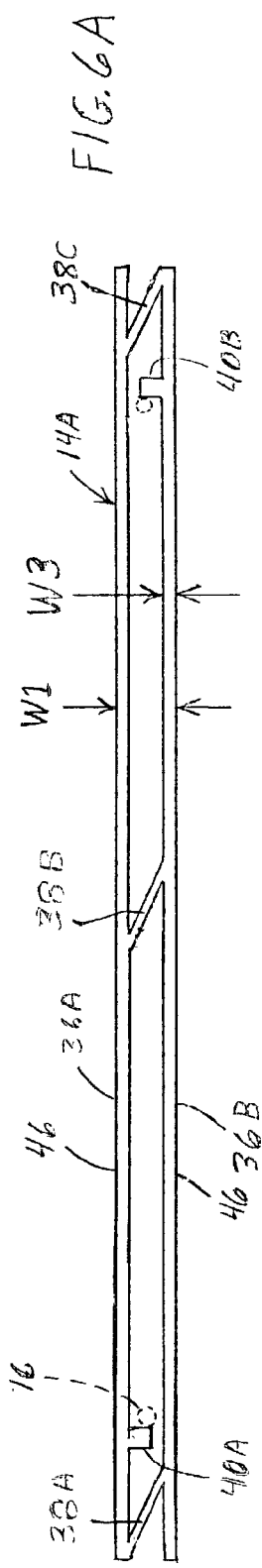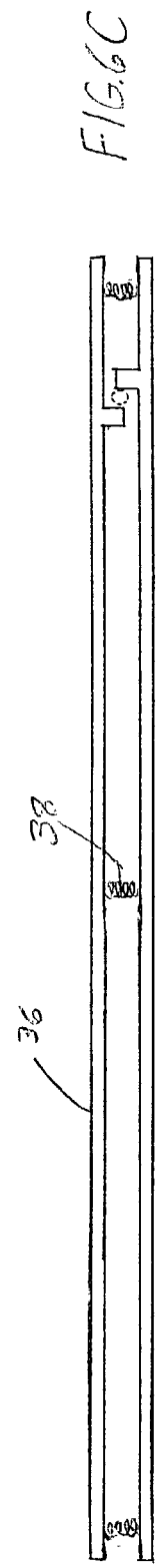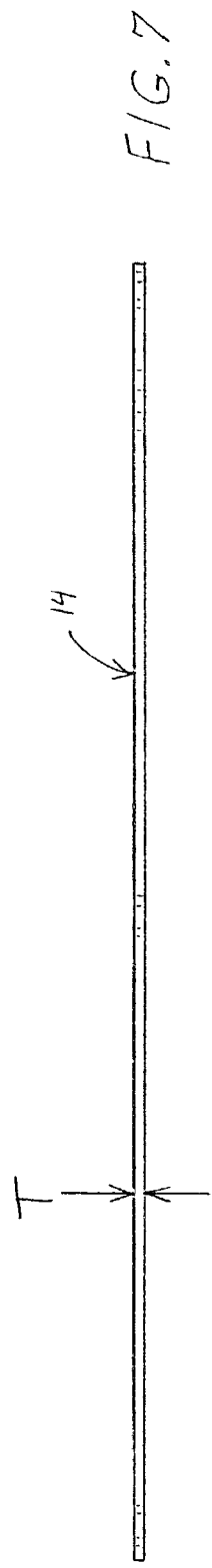

BONE SUPPORT ASSEMBLY

BACKGROUND

The present invention relates to devices for the fixation and/or support of bones. In particular, the present invention relates to a bone support assembly, and a corresponding bone support plate, for the fixation and/or support of bones of the spinal column. The plate of the present invention has particular application in situations where compressional or "settling" forces, as well as torsional and flexing forces, of "fixed" vertebrae on a spinal plate cause significant stressing and potential failure of the spinal plate and/or plate components.

Vertebral fixation has become a common approach to treating spinal disorders, fractures, and for fusion of vertebrae at the time such fixation is instituted. Namely, one or more vertebrae are fixed in position relative to one or more other vertebrae above and/or below the vertebrae to be fixed. Generally, a spinal plate is the device of choice used for mechanically supporting such vertebral fixation. A typical spinal plate includes a plate having a plurality of apertures therethrough. A corresponding plurality of fasteners, i.e., bone screws, are generally positioned into and through respective apertures of the plate to secure the spinal plate to a bone, such as two respective upper and lower supporting adjacent spinal vertebrae. The screws are fastened to the respective support vertebrae to secure the spinal plate to the respective vertebrae. In general, such plate and screw assemblies can be utilized, generally, for anterior fixation of the spine for cervical, lumbar, and/or thoracic fixation.

The basis of anterior fixation or plating is to approach the spine from an anterior or anterio-lateral approach, and use the screws to solidly mount the spinal plate to the affected vertebrae. Often, in addition to the application of a spinal plate, graft material may be combined in an attempt to permanently fuse together adjacent vertebrae. The graft material can consist of bone grafts obtained from bones of the recipient or another individual.

A common problem associated with the use of such spinal plates is the tendency of the bone screws to "back out" or pull away or withdraw from the bone into which they are fixed. This problem occurs, primarily, due to the normal torsional and bending motions of the body and spine. This is a particularly important problem because as the screws become loose and pull away or withdraw from the bone, the heads of the screws can rise above the surface of the spinal plate and, possibly, even work their way completely out of the bone. While this condition can cause extreme discomfort for the recipient, this condition can also create a number of potentially serious physiological problems given the significant amount of nervous and vascular structures associated at or near the potential locations of anterior spinal plate fixations.

A number of designs have been proposed in attempts to prevent screws from pulling away or withdrawing from the bone and/or to prevent the screws from backing out or pulling away or withdrawing from the surface of the spinal plate. Such mechanisms used to prevent bone screws from pulling out of bones include cams which engage and lock the screws, and the use of expanding head screws which expand outwardly when adequate force is applied thereto to engage the holes in the spinal plate. All of these designs have detriments including potential for breakage or requiring particular precision and alignment in their application in order to work correctly. Additionally, loose components and accessories of spinal plates which address the "backing-out" or withdrawal problem can get dropped and/or misplaced while the vertebral fixation surgical procedure is taking place, prolonging and complicating the procedure as well as creating substantial risk of harm to the recipient.

Yet another common problem associated with the use of such spinal plates is the tendency of the vertebrae being "fixed" to settle after spinal plate insertion adding compression forces to the above-listed forces which cause the bone screws to "back out" or pull away or withdraw from the bone into which they were fixed.

It is an object of the invention to provide bone support assemblies which provide rigid bone-to-bone fixation and/or support, such as e.g. adjacent or second adjacent vertebrae, while allowing post-procedural compression between the respective bones.

It is another object of the invention to provide bone support assemblies which afford substantial protection against pulling away or withdrawal of affixing components which may result from torsional movement, flexing movement, or stress and/or dynamic load sharing of the vertebrae, thereby enhancing the bone rebuilding process.

It is yet another object of the invention to provide bone support assemblies which attenuate application of stress on the apparatus and affixing components.

It is a further object of the invention to provide bone support assemblies comprising a bone support plate and resiliently flexible bands so mounted and positioned to enable bone fasteners to pass such bands, with corresponding flexing or other movement of such bands, when the bone fasteners are being installed in a recipient and which, in combination with the designs of the bone fasteners, prevent withdrawal of such bone fasteners after installation in the recipient.

It is yet a further object of the invention to provide bone support assemblies which can be completely pre-assembled such that no assembly steps need be performed on the bone support assembly, itself, while the bone support assembly is being installed in a recipient thereof.

It is still a further object of the invention to provide bone support assemblies wherein apparatus, in such bone support assemblies, for preventing withdrawal of bone fasteners from the bone, after installation on a recipient, are automatically activated, to prevent such withdrawal, as a consequence of the installation of suitably-configured such bone fasteners.

SUMMARY

This invention provides novel bone support assemblies, methods of fabrication of such bone support assemblies, and methods of use of such bone support assemblies. Such bone support assembly comprises a locking structure assembled to a bone support plate. The locking structure comprises first and second elongate bands biased against each other by at least first and second springs. The elongate bands are juxtaposed proximate, and extend into, fastener-receiving-apertures in the bone support plate. The bands are effective, automatically and as a consequence of driving of a bone fastener through the respective aperture, to respond to a side force applied by an interfering element of the bone fastener by resiliently moving transversely of the band away from the interfering element, and by resiliently returning to a blocking position over the interfering element after the interfering element passes the band.

In a first family of embodiments, the invention comprehends a bone support assembly. The bone support assembly comprises a bone support plate. The bone support plate comprises a top surface, a bottom surface opposite the top surface and adapted to engage bone structure of a recipient, first and second side surfaces, and a plurality of bone-fastener-receiving apertures extending between the top surface and the bottom surface for receiving bone fasteners therethrough for securing the bone support assembly to the bone structure of the recipient. The bone support plate further comprises a length and a width, and a thickness between the top surface and the bottom surface, channel structure extending alongside respective ones of the apertures and generally aligned with the top surface of the bone support plate. The channel structure comprises at least one channel having a length, a width, a bottom, and first and second sides. At least one of the first and second sides of the at least one channel has an opening therein extending into a respective one of the apertures. The invention further comprises locking structure in respective ones of the at least one channel. The locking structure in a given channel has a length, and comprises first and second elongate bands having respective lengths, and extending along the length of the respective channel. At least one resilient spring, preferably at least two springs, extend between, and connect, the first and second elongate bands, thus biasing the bands against each other and urging the first and second bands into engagement with the first and second sides of the respective channel. One of the first and second bands extends through at least one of the openings in the respective side of the channel, and thus extends into and across a portion of a respective aperture. The band is effective, automatically and as a consequence of driving a bone fastener through the respective aperture and into bone structure of a recipient, to respond to a side force applied by an interfering element of the bone fastener by resiliently moving transversely of the length of the respective band, and away from the interfering element, and by resiliently returning to a blocking position over the interfering element after the interfering element passes the band, whereafter the position of the band over the interfering element is effective to automatically inhibit withdrawal of the bone fastener, past the band, and out of the bone support assembly.

In preferred embodiments, the first and second bands comprise resiliently flexible bands, with lengths of the bands extending alongside corresponding ones of the apertures whereby, as a bone fastener is driven, a break structure of such bone fastener urges the band to automatically flex transversely of the length of the band, from a first flexural condition, until such break structure in such bone fastener is driven past the band, whereupon the band resiliently returns substantially to the previous flexural condition and overlies the break structure of the so-driven bone fastener and thereby prevents the bone fastener from withdrawing the break structure past the band.

In preferred embodiments, the at least one channel extends along the length of the bone support plate past at least a first row of the apertures and opens into each of the bone-fastener-receiving apertures in the respective row.

In some embodiments, all of the bone-fastener-receiving apertures comprise circular projected openings, and thus have substantially equal projected lengths and projected widths.

In other embodiments, at least all except two of the bone-fastener-receiving apertures have greater lengths, along the length of the bone support plate, than widths transverse to the length of the bone support plate, and thereby comprise slots, enabling longitudinal movement of bone fasteners in the slots, with respect to the bone support plate, thereby to accommodate settling of respective bones to which and adjacent which the bone support assembly is affixed.

In yet other embodiments, all of the bone-fastener-receiving apertures comprise slots, having lengths greater than respective widths of the respective slots.

In preferred embodiments, first and second rows of the bone-fastener-receiving apertures extend along the length of the bone support plate, the at least one channel comprising a channel extending along the length of the bone support plate, sides of the channel opening into each aperture in the first and second rows of apertures, the first and second elongate bands being urged against the respective first and second sides of the channel, the first elongate band extending into and across portions of respective apertures in the first row, the second elongate band extending into and across portions of respective apertures in the second row.

In preferred embodiments, the at least one resilient spring comprises at least two compression springs extending between the first and second bands.

In highly preferred embodiments, the first and second bands, in combination with the springs, define a unitary structure derived from a single unitary work piece.

In preferred embodiments, the first and second bands extend along substantially the entirety of the full lengths of respective first and second sides of the channel, the first and second bands collectively extending into and across portions of each of the bone-fastener-receiving apertures.

Further to preferred embodiments, the bone support plate comprises first and second rows of bone-fastener-receiving apertures extending along the length of the bone support plate, the at least one channel comprising a channel extending along the length of the bone support plate, and first and second overhanging top walls of the channel extending inwardly from the sides of the channel and spaced from each other, thereby leaving an opening in the top of the channel between the overhanging top walls and extending along the length of the channel, the overhanging top walls being effective as retainers to restrain movement of the locking structure out of the channel through the top of the channel.

In preferred embodiments, the locking structure further comprises first and second band retainers extending from at least one of the first and second bands, each band retainer on a respective band extending inwardly toward the other band, and at least one stud extending into the channel and interacting with the band retainers so as to prevent substantial longitudinal movement of the locking structure along the length of the channel.

In preferred embodiments, the first and second elongate bands are urged, by the at least one resilient spring, against the respective first and second sides of the channel, and thus into and across a portion of each respective aperture in the first and second rows.

In some embodiments, the first and second band retainers are substantially spaced longitudinally from each other along the length of the locking structure, and interact with first and second respective studs spaced from each other, the studs being disposed adjacent respective ones of the retainers so as to prevent substantial movement of the locking structure along the length of the channel.

In other embodiments, the first and second band retainers are closely spaced longitudinally with respect to each other, and interact with a common stud, on opposing sides of the stud, so as to prevent substantial movement of the locking structure along the length of the channel.

In some embodiments, the first and second bands comprising substantially non-resilient bands, the lengths of the bands extending alongside corresponding ones of the apertures whereby, as a such bone fastener is driven, a break structure of such bone fastener urges the band to automatically move from a first position transversely of the length of the band, with corresponding flexing of the at least one resilient spring, from a first flexural condition, until such break structure in such bone fastener is driven past the band, whereupon the spring resiliently returns the band to substantially the first position, whereupon the band overlies and blocks the break structure of the so-driven bone fastener and thereby prevents the bone fastener from withdrawing the break structure past the band.

In preferred embodiments, the at least one spring comprises at least two springs extending as compressible folded leaves between the first and second bands.

In preferred embodiments, the compositions of the first and second bands comprise predominantly nickel and titanium, whereby the first and second bands are resiliently flexible bands.

Preferably, the compositions of the first and second bands comprise about 55 percent by weight to about 56 percent by weight nickel and about 44 percent by weight to about 45 percent by weight titanium.

In highly preferred embodiments, the compositions of the first and second bands comprise shape memory metal alloys comprising predominantly nickel and titanium.

In some embodiments, the compositions of the bands are selected from the group consisting of titanium and stainless steel.

In other embodiments, the compositions of the flexible bands are not shape memory metal alloys, and the bands are sufficiently small in cross-section, and are properly positioned over the apertures, so as to let a bone fastener pass below a respective band, with transverse movement of the band, and without exceeding a flexural limit of the at least one spring, such that the spring then returns the band to a blocking position over the bone fastener.

In preferred embodiments, the at least one resilient spring comprises a substantially straight line angle compression spring, preferably three substantially straight line angle compression springs, integral with the first and second bands, and wherein the spring, in combination with the first and second bands, defines a unitary structure derived from a unitary work piece.

In some embodiments, the bone-fastener-receiving apertures comprise pairs of the apertures spaced along the length of the bone support plate, the channel structure comprising an elongate channel extending along the length of the bone support plate, the locking structure comprising a plurality of band structures positioned in the channel, disposed lengthwise of each other, and disposed alongside the respective pairs of apertures, and spacers being positioned between respective adjacent band structures so as to inhibit substantial longitudinal movement of the band structures, the spacers optionally being held in position in the channel by studs extending through the bone support plate and into the channel, and into cooperating apertures in the respective spacers.

In a second family of embodiments, the invention comprehends a method of fabricating a bone support assembly. The method comprises providing a bone support plate having a top surface, a bottom surface opposite the top surface and adapted to engage bone structure of a recipient, and having first and second sides, and a plurality of bone-fastener-receiving apertures extending between the top surface and the bottom surface for receiving bone fasteners therethrough for securing the bone support assembly to such bone structure of such recipient. The bone support plate further comprises a length and a width, and a thickness between the top surface and the bottom surface, and a channel extending along the length of the bone support plate. The channel has a length, a bottom, a top, and first and second sides. The sides of the channel have openings therein extending into respective ones of the bone-fastener-receiving apertures. The channel has an opening on at least one end of the bone support plate. The method comprises inserting longitudinally into the channel, through the end opening, a locking structure, the locking structure having a length and comprising first and second bands connected to each other by a plurality of spaced resiliently compressible springs urging the first and second bands into engagement with the first and second sides of the channel when the locking structure is in the channel, whereby the first and second bands extend into, and across, portions of the bone-fastener-receiving apertures; and extending one or more locking studs through structure of the bone support plate and into the channel transverse to the length of the locking structure and engaging the locking structure so as to inhibit, preferably prevent, substantial movement of the locking structure along the length of the channel.

In some embodiments, the bone support plate defines first and second overhanging top walls of the channel, extending inwardly from the sides of the channel and spaced from each other, and the overhanging top walls are effective as retainers to restrain movement of the locking structure out of the channel through the top of the channel.

In a third family of embodiments, the invention comprehends a method of installing a bone support assembly in a recipient thereof. The method comprises providing a bone support assembly comprising a bone support plate having a top surface, a bottom surface opposite the top surface and adapted to engage bone structure of a recipient, and a plurality of bone-fastener-receiving apertures extending between the top surface and the bottom surface for receiving bone fasteners therethrough for securing the bone support assembly to such bone structure of such recipient, the bone support plate further comprising a length and a width, and a thickness between the top surface and the bottom surface, and a channel extending along the length of the bone support plate, the channel having a length, a bottom, a top, and first and second sides, the sides of the channel having openings therein extending into respective ones of the bone-fastener-receiving apertures, the channel having an opening on at least one end of the bone support plate; and a locking structure in the channel, the locking structure having a length and comprising first and second bands connected to each other by a plurality of spaced resiliently compressible springs, biasing the first and second bands against each other and urging the first and second bands into engagement with the first and second sides of the channel when the locking structure is in the channel, whereby the first and second bands extend into, and across, portions of the bone-fastener-receiving apertures; and locking studs extending through structure of the bone support plate and into the channel transverse to the length of the locking structure and engaging the locking structure so as to prevent substantial movement of the locking structure along the length of the channel. The method further comprises advancing bone fasteners through selected ones of the bone-fastener-receiving apertures and into bone structure of the recipient thereof, including advancing interfering elements of the bone fasteners past respective elements of the first and/or second bands, such that a given interfering element causes the respective band to deflect from a first position, transversely of the length of the band as the interfering element passes and such that, when the interfering element moves past the band, the band returns to the first position, thereby occupying a blocking position whereby the interfering element is effective to automatically inhibit withdrawal of the bone fastener, past the band.

BRIEF DESCRIPTION OF THE DRAWINGS

FIG. 6A shows a top view of a first embodiment of locking structures which are incorporated into bone support assemblies of the invention, and wherein the longitudinal retainers are substantially spaced from each other, and extend from opposing bands.

FIG. 6B shows a top view of a second embodiment of locking structures which are incorporated into bone support assemblies of the invention, and wherein the longitudinal retainers are closely spaced from each other, and extend from opposing bands.

FIG. 6C shows a top view of a third embodiment of locking structures which are incorporated into bone support assemblies of the invention, wherein the longitudinal retainers are closely spaced from each other and extend from opposing bands, and wherein the spring feature is represented by coiled compression springs.

FIG. 7 shows a side elevation of the locking structure of FIG. 6A.

Figure 1:
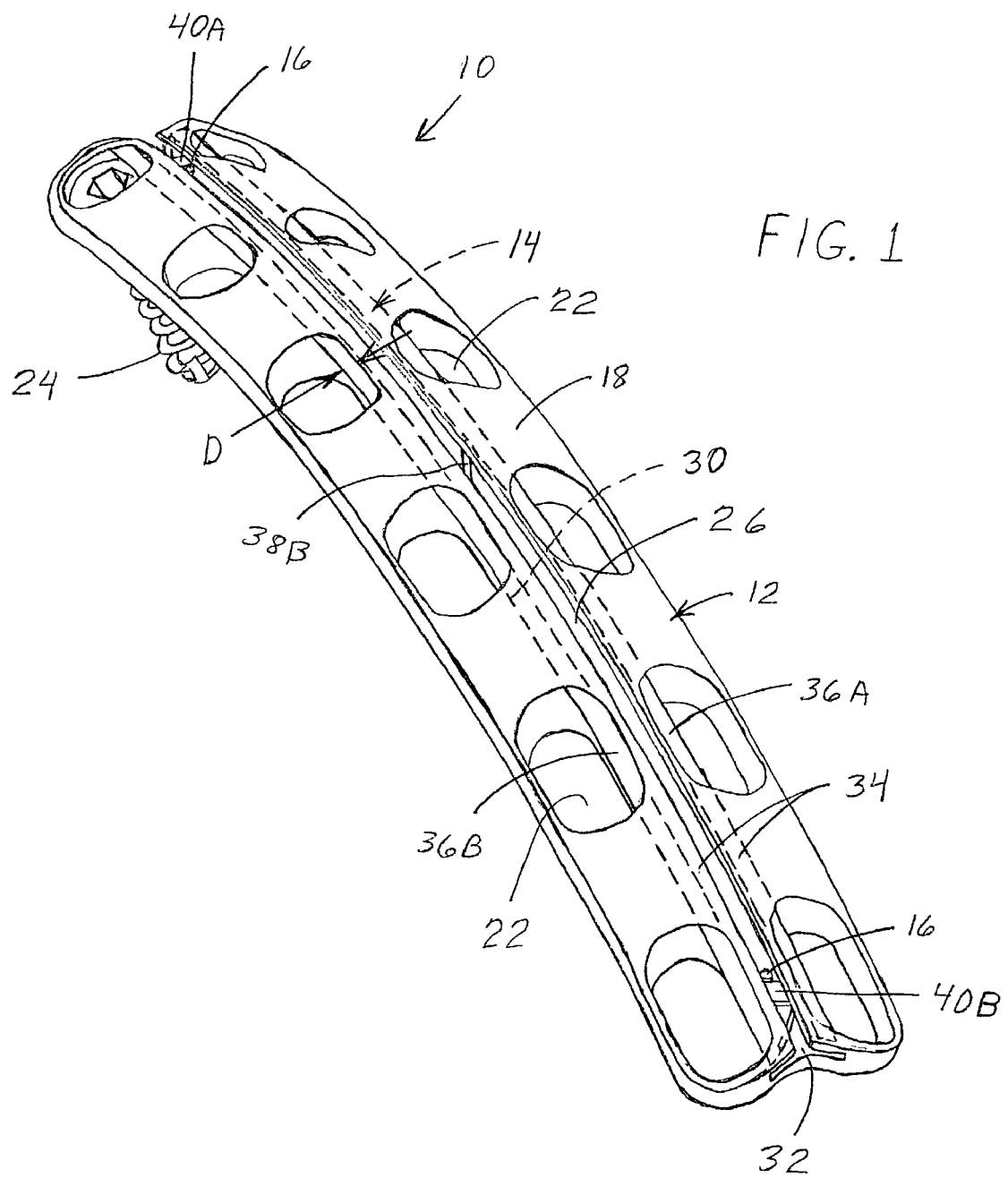
FIG. 1 shows a pictorial view of a first embodiment of bone support assemblies of the invention, including a bone support plate.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Referring now to the embodiments represented by FIGS. 1–5, a bone support assembly 10 of the invention includes a bone support plate 12, a locking structure generally represented by 14 in FIG. 1, and one or more retaining studs 16.

Bone support plate 12 has a top surface 18, a bottom surface 20, and a plurality of bone-fastener-receiving apertures 22 which receive bone fasteners such as bone screws 24. Apertures 22 are arranged in first and second rows of such apertures, along the length of the bone support plate.

Top surface 18 of the bone support plate defines a channel 26 extending along the length of the support plate. Channel 26 has a bottom wall 28, opposing side walls 30, and has openings 32 extending out the respective ends of support plate 12, best seen in FIG. 5. An opening 32 is illustrated in FIG. 1. Channel 26 further has overhanging top walls 34 extending inwardly from the side walls of the channel and spaced from each other, thereby leaving an opening 35 in the top of the channel between the overhanging top walls and extending along the length of the channel. The open cross-section of the channel, as defined between side walls 30 and top and bottom walls 28 and 34, is preferably consistent along substantially the full length of the support plate. Side walls 30 of the channel are specifically located and configured so as to open into the sides of, and extend along and inwardly of the sides of, apertures 22. In general, imaginary extensions of side walls 30 project across apertures 22 at locations displaced inwardly of the aperture side walls by distance "D" of about 1 mm.

FIG. 6A illustrates the locking structure 14A which is incorporated into the assembly illustrated in FIG. 1. As seen in FIG. 6A, locking structure 14A includes first and second elongate bands 36A, 36B extending parallel with each other and in a common plane. Bands 36A, 36B are connected to each other by three substantially straight line compression springs 38A, 38B, 38C mounted to bands 36A, 36B at straight line angles of about 10 degrees to about 30 degrees to the respective bands. First and second band retainers 40A, 40B extend from the respective bands 36A, 36B, toward the opposing bands. Thus, retainer 40A is disposed proximate the left end of band 36A and extends toward band 36B. Correspondingly, retainer 40B is disposed proximate the right end of band 36B and extends toward band 36A.

Leaf springs 38A, 38B, 38C represent only one of a wide variety of options regarding compression spring loading of the bands for biasing the bands against each other and thus for displacement of the bands away from each other. While 3 springs are shown, any number of springs can be used, with suitable adjustment of the force exerted by each spring.

Referring to FIGS. 1 and 6A, first and second retainer studs 16 extend, by friction fitment, through apertures 44 in the bottom wall of support plate 12, and thence into channel 26 and into abutment with band retainers 40A, 40B. Studs 16 are shown in solid outline in FIG. 1, and are shown, to illustrate their relative locations, in dashed outline in FIG. 6A.

The width "W1" of locking structure 14 between the outer walls 46 of bands 36A, 36B is slightly greater at rest than the width "W2" of channel 26 between side walls 30. Locking structure 14 is inserted longitudinally into channel 26 by squeezing the locking structure together at the width dimension thereof, at least at an end of the locking structure, sufficient to reduce the width "W1" of the locking structure to a width less than width "W2" of channel 26; and by inserting the reduced-width squeezed end of the locking structure into the opening at the end of channel 26. As the locking structure is squeezed, the squeezing is progressively resisted by the resilience of the compression springs 38A, 38B, 38C between the bands. The spring closest to the end being squeezed together is most effective in resisting such squeezing, thereby setting up a resilient force urging restitution of the compressive squeezing force, and thus urging the outer walls 46 of the locking structure into engagement with side walls 30 of the channel as the locking structure is being inserted longitudinally into channel 26. As the insertion of the locking structure progresses into channel 26, the respective compression springs 38 become progressively squeezed as they enter channel 26, each developing a desirable resilient outwardly-directed force urging the outer walls 46 of the bands into engagement with side walls 30 of the channel.

Since the side walls of the channel open into apertures 22, bands 36A, 36B extend across apertures 22 as the locking structure is inserted into channel 26. The length of locking structure 14 generally corresponds substantially with the length of channel 26 such that the entirety of the length of the locking structure is received within channel 26, and wherein the locking structure extends substantially the full length of channel 26. The length of the locking structure should be at least great enough that bands 36A, 36B extend across each of the apertures 22 in the respective row of apertures.

Once the locking structure is thus installed in channel 26, retainer studs 16 are inserted through apertures 44 into channel 26. Studs 16 are sized to friction fit into apertures 44, and can be welded to plate 12 e.g. at the bottom surface of plate 12 if desired. Studs 16 extend into channel 26 a distance sufficient to come into close proximity with, optionally to come into abutting engagement with, band retainers 40A, 40B. In the embodiment illustrated in FIGS. 1 and 6A, the studs are between the two band retainers 40A, 40B, whereby the respective studs effectively interact with the band retainers so as to prevent substantial longitudinal movement of the locking structure along the length of the channel. Thus, with the studs installed, the locking structure is restrained from moving longitudinally along the length of the channel. At the same time, the bands 36A, 36B are being urged against the side walls of the channel by springs 38.

Locking structure 14, including bands 36A, 36B, is thus effectively confined in channel 26. The locking structure is effectively prevented from moving longitudinally by studs 16. The locking structure is effectively prevented from moving laterally by side walls 30 of the channel. The locking structure is effectively prevented from moving vertically by bottom wall 28 and overhanging top walls 34. Thus, once the locking structure is inserted into the channel, and the studs 16 are installed in interfering relationship with retainers 40A, 40B, the locking structure is effectively locked into position in channel 26. In such position, bands 36A, 36B extend across portions of the respective apertures 22 as illustrated in e.g. FIGS. 1–3.

As shown in the various drawings, springs 38 extend between the respective bands 36A, 36B, and thus bias the bands with respect to each other. Thus, e.g. when squeezing force is applied to the locking structure to reduce the overall width of the locking structure thereby to enable the locking structure to be inserted into channel 26, springs 38 are effectively biasing the bands against each other, such that a force exerted against a first one of the bands, and directed toward the other of the bands, is transferred at least in part to the other band, whereby the physical properties of the bands interact with each other when such force is applied.

Thus, springs 38 position bands 36 solidly against the side walls of the channel where the bands are not passing through apertures 22. With the bands solidly against the side walls of the channel, the outwardly-disposed walls 46 of the bands are in surface to surface contact with side walls 30 of the channels. The outwardly-disposed walls 46 of the bands, the spring-loading of the bands, the respective rows of apertures 22, overhanging top walls 34, and springs 38 are thus correspondingly sized, arranged and configured with respect to each other such that bands 36 are trapped between the side walls, the channel bottom, the overhanging top walls, and the springs such that the bands, without external forces applied, extend along a path wherein outwardly-disposed walls 46 of the bands extend along side walls 30 of the channel. Since imaginary extensions of the side walls are displaced inwardly of the aperture side walls by about 1 mm, the outwardly-disposed side walls of the bands also are displaced inwardly of the aperture side walls by the distance "D" of about 1 mm, and thus extend across corresponding portions of the projected cross-sections of the respective apertures.

FIG. 6B illustrates a second embodiment of the locking structure wherein the band retainers are spaced closely adjacent each other, with a single locking stud 16, shown in dashed outline, interposed between the band retainers. The spacing between the band retainers is only great enough to enable stud 16 to be inserted between the retainers. Thus, the stud is either in frictional engagement with both retainers, or is so close to both retainers that no more than negligible longitudinal movement can be effected by locking structure 14 after the locking structure is installed in channel 26, and stud 16 is installed between the retainers.

Whether the retainers are closely spaced as in FIG. 6B or are substantially spaced from each other, e.g. proximate ends of the locking structure, either retainer 40A, 40B can extend from either of the bands 36A, 36B. FIGS. 6A and 6B show one such retainer from each such band 36A, 36B. In the alternative, both retainers can extend from either band 36A or 36B.

Similarly, the position or positions of the stud or studs, with respect to the retainers is not critical so long as the overall effect is that interaction of the retainers with the stud or studs prevents the locking structure from moving either longitudinal direction in the channel. For example, FIG. 6A shows the studs both being disposed longitudinally inwardly of the retainers. The studs can as well both be disposed longitudinally outwardly of the retainers.

Springs 38 can employ a variety of spring structures and still perform effectively. Thus, FIGS. 6A and 6B show substantially straight line angle compression springs which typically define angles of about 10 degrees to about 30 degrees with the respective bands. Angles of about 15 degrees to about 20 degrees are preferred. Such springs are also known as "N" springs wherein the legs of the "N" are represented by bands 36A and 36B, and wherein the angled "N" connector extends between the two bands.

The magnitude of the angle, in combination with the magnitude of the cross-section, in combination with the composition, of a spring 38 at least in part determines the spring constant, whereby any of the respective determinant parameters can be modified according to conventional knowledge in obtaining the desired spring constant, wherever advantage is to be obtained.

Figure 10:
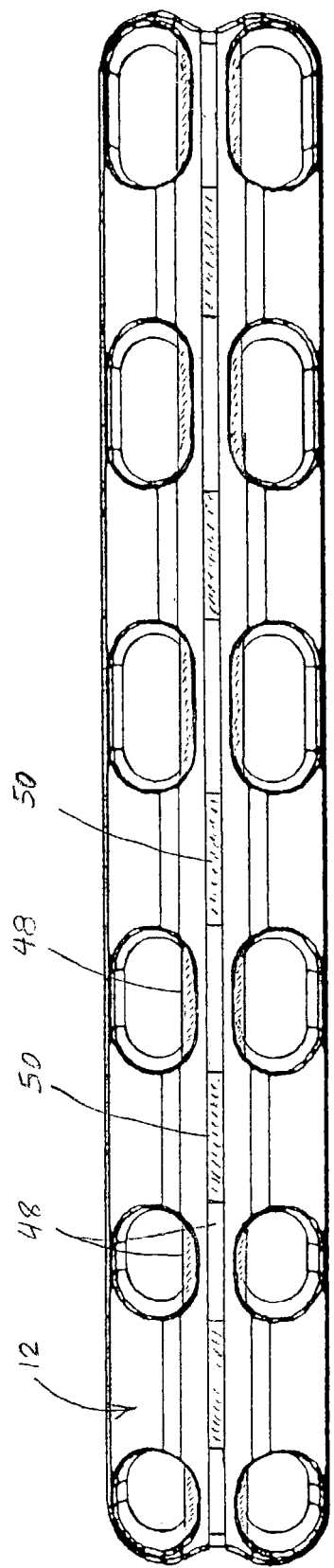
FIG. 10 is a top view of a bone support assembly of the invention employing a segmented locking structure and slot-shaped apertures.
Figure 11:
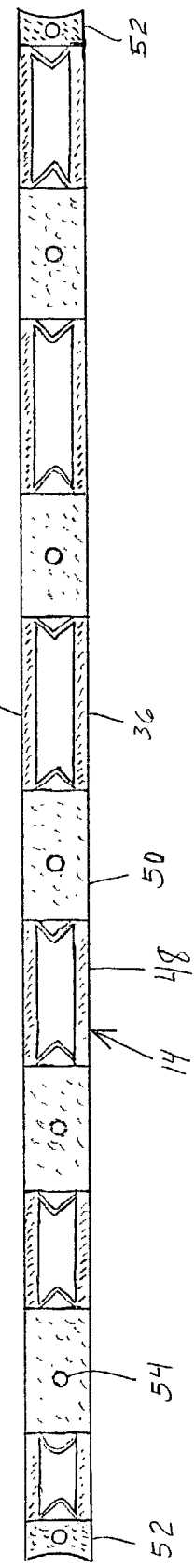
FIG. 11 shows a bottom view of the segmented locking structure of FIG. 10, separated from the bone support plate.

Springs 38 need not be straight line constructs. Rather, such springs can embody, for example and without limitation, a number of curvilinear shapes and angular shapes. Indeed a folded leaf construct is shown in FIGS. 10 and 11, as discussed further hereinafter. All that is required is that the spring provide the desired restitution force and distance of movement to bands 36A, 36B to accommodate installation of locking structure 14 into channel 26, and passage of fasteners 24 accompanied by resilient restoration of the bands over the heads of the fasteners, whereby a wide range of spring structures are suitable for use as springs 38.

As an exemplary alternative, FIG. 6C shows coil springs. As other alternatives, one can thus select from a wide range of conventionally available springs for use as springs 38.

FIG. 7 shows a side view of the locking structure, illustrating the preferred uniform thickness "T" of the locking structure along the length of the locking structure.

Figure 8:
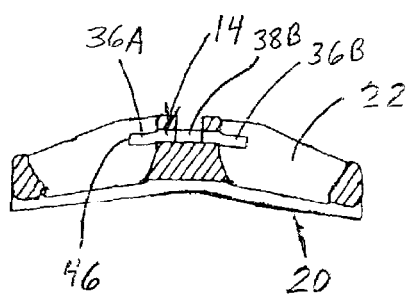
FIG. 8 shows a cross-section of the bone support assembly of FIGS. 1–4 and is taken at 8—8 of FIG. 4.
Figure 5:
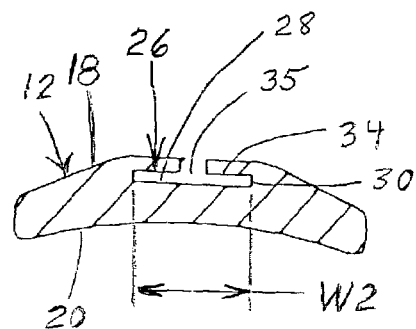
FIG. 5 shows a cross-section of the bone support plate illustrated in FIGS. 1–4, and is taken at 5—5 of FIG. 4.

FIG. 8 shows a cross-section of the bone support assembly of FIGS. 1–4 at an aperture 22. Thus, FIG. 8 shows bands 36A, 36B extending into the projected cross-section of apertures 22, as well as showing spring 38B biasing the bands into such position.

Figure 9A:
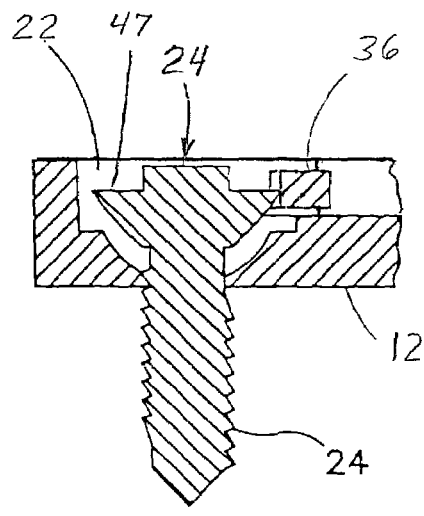
FIG. 9A is a cross-section of a bone support assembly as in FIGS. 1–4, showing the band deflected by the passing of the break structure, on the head of a bone screw, in contact with the band.
Figure 9B:
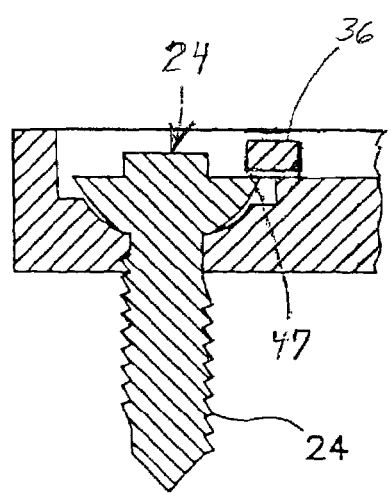
FIG. 9B is a cross-section as in FIG. 9A wherein the head of the bone screw has passed the bottom of the band thus to enable the band to revert to its undeflected and blocking position over the head of the bone screw.

FIGS. 9A and 9B illustrate the process by which a band 36 is deflected when a bone screw 24 passes the band, and further illustrate the interference in a withdrawal path of the screw, provided by the band after the screw has been driven past the band and the band has returned to the undeflected condition.

Referring to FIG. 9A, as a bone screw is advanced through an aperture 22, the spring biasing of the band is effective, automatically and as a consequence of driving the bone screw through the respective aperture and into bone structure of a recipient, to respond to side force applied by an interfering element 47 such as the outer portion of the head of the bone screw by resiliently moving transversely of the length of the band, and away from such interfering element, and by resiliently returning to a position over the interfering element after the interfering element passes the band. After returning over the interfering element, the position of the band over the interfering element is effective to automatically inhibit withdrawal of the bone screw past the band and out of the bone support assembly.

Looking specifically at FIG. 9A, as the bottom surface (e.g. interfering element) of the outer portions of the head of the bone screw engages the top outer corner of the band, the beveled or conical bottom surface of the screw head urges the band out of interfering alignment under the screw head. Once the screw head, as an interfering element of the screw, has moved past the band, the band automatically returns into an interfering, blocking position over the outer edge of the screw head as shown in FIG. 9B. Such interfering, blocking position over the screw head is effective to interfere with, typically to block, withdrawal of that screw past that band. Thus, the band serves as a safety device preventing withdrawal of the bone screw from the bone, and from the bone support assembly.

FIGS. 10 and 11 illustrate a further family of embodiments of bone support assemblies of the invention. In the embodiments of FIGS. 10 and 11, plate 12 is substantially as shown and described in the previous embodiments. However, locking structure 14 is shown as a plurality of shortened band-spring combinations 48, with spacers 50 disposed between the respective band-spring combinations, and with end closures 52 at respective outer ends of the outer-most ones of the band-spring combinations. Stud apertures 54 are shown in the bottom surfaces of spacers 50 and closures 52. Corresponding stud apertures 44 are also employed in plate 12 extending from the bottom surface of plate 12 to the bottom of channel 26. Studs are inserted through apertures 44 and into corresponding apertures 54, thus to fix the longitudinal positioning of the spacers and end closures. Where desired, less than all, in fact, none, of the spacers need employ such studs, since the spacers and band-spring combinations are effectively held in the channel by the studs employed at end closures 52.

Thus, FIGS. 10 and 11 illustrate a plurality of band-spring combination structures positioned in the channel and disposed alongside the respective pairs of apertures, with spacers positioned between respective adjacent band structures so as to inhibit substantial longitudinal movement of the band structures, and to provide continuous end surfaces, at the ends of the spacers, against which the spacers can flex inwardly as a bone screw is driven past the respective band. As shown, each band-spring combination includes a pair of bands 36 on opposing sides of the combination element, and first and second 2-direction leaf springs at opposing ends of the combination element.

The spacers are held in position in the channel by studs extending through the bone support plate and into the channel, and into cooperating apertures in the respective spacers.

FIGS. 10 and 11 show a separate band-spring combination 48 deployed adjacent each pair of apertures 22. As desired, fewer such band-spring combinations can be used wherein at least one such band-spring combination can extend across two or more such pairs of apertures.

Since bone support assemblies of the invention are to be used within living bodies, all materials used in the bone support assemblies must be compatible with, and safe for use inside, the living body. In that regard, preferred material for bone support plate 12 locking structure 14, springs 38, and studs 16, is titanium. Preferred compositions for bands 36 having a desired level of resilient flexural capability are shape memory metal alloys, also known as superelastic alloys. Such metals are well known for the ability to tolerate levels of flex which are extraordinary for metals, and to automatically and resiliently return to a pre-flex configuration or condition when the flexing force is released. For example, a strip of such material may have e.g. a straight or generally linear rest condition or configuration; and can be bent, twisted, distorted, and otherwise reconfigured under reconfiguring force and, when the force is removed, will return to the rest configuration or condition, or to a configuration or condition very near to the rest condition or configuration.

Typical shape memory metal alloy bands or superelastic bands are about 50 weight percent to about 60 weight percent nickel and respectively about 50 weight percent to about 40 weight percent titanium, preferably about 55 weight percent to about 56 weight percent nickel and conversely about 45 weight percent to about 44 weight percent titanium. Suitable band materials, containing about 55.8 weight percent nickel and correspondingly about 44.2 weight percent titanium, are available from NDC Company, Wayzata, Minn. as NITINOL SE 508. A typical band 36 made of such NITINOL, and for use in bone support assemblies used in adults has a width "W3" of 0.04 inch (1 mm) and a thickness"T1", which corresponds to thickness "T" of the locking structure, of about 0.016 inch (0.4 mm). Similarly, springs 38 can well be made of such resiliently flexible NITINOL or other flexible metal composition, and preferably have the same, or a similar, thickness.

While shape memory metal alloys are preferred for use in bands 36 and springs 38, other materials can be used so long as such materials meet the requirements of the use environment. Namely, such materials must be safe for use in the living body. Safety is typically controlled by composition and structure. In this analysis, exemplary structure is shown in the drawings herein; and composition is the variable being analyzed.

In addition, such materials, even though not known as shape memory metal alloys, must perform the required physical functions of flexing enough, when properly positioned over apertures 22, to let the bone screws pass below the bands without exceeding the flexural limits of the band materials or the springs, and must return to blocking positions over the screws after passage of the bone screws. Such flexural properties are based on physical properties inherent in the material compositions, in combination with the physical cross-sections of the bands and springs.

The resilient properties can be provided by either bands 36, springs 38, or a combination of bands 36 and springs 38. Thus, bands 36 can be substantially non-flexible and substantially all the resilience can be provided by the flexibility of springs 38. In the alternative the springs can be substantially non-flexible and substantially all the resilience can be provided by bands 36.

In preferred embodiments, bands 36 and springs 38 are machined from a single piece of material whereby the inherent physical properties of the bands and the springs are the same. Typically, the resilience in such combination is provided by the combination of springs 38 and bands 36. The resiliences provided by the respective bands and springs in such combination is nevertheless dependent on the respective widths of the bands and springs, as well as on the angles expressed between the spring leaves and the bands at any given time. Thus, the springs and bands can be engineered for a wide range of desired degrees of resilient restoration force to be provided by the respective bands and springs.

Accordingly, certain materials which are not known as shape memory materials can, when fabricated into sufficiently small cross-sections, perform the desired resiliently flexural function of especially the springs or the bands. Applicant contemplates that bands 36 can thus employ titanium compositions or stainless steel compositions, as alternatives to the shape memory e.g. NITINOL compositions mentioned above. Other materials can be used so long as such materials satisfy the above safety and performance requirements.

As a result of the structures of apertures 22, channel side walls 30, and locking structure 14, along with proper positioning of stud 16, when a bone screw, which properly fits the apertures 22, is driven through an aperture 22, the head of the bone screw impacts the respective band 36 as shown in FIG. 9A, and forces the band in a width-wise transverse direction away from the center of the aperture in order that the head of the bone screw can pass the band. Since the band is readily and resiliently moved, against resistance of springs 38, the band moves in response to the urging of the head of the bone screw, as shown in FIG. 9A. When the head of the bone screw passes below the bottom of the band, the band is no longer being held in the moved position, and returns to the position occupied prior to being moved, thereby setting up a potential interference between the band and the screw, of more or less 1 mm, which interference is activated if and when the screw begins to back out of, or withdraw from, the bone plate.

The invention contemplates that bands 36 can be arranged in other than a rest, or straight, condition when not being forced sideways. Thus, the bands can be under a degree of constant stress, which changes, either increase or decrease, as the head of the screw passes, and then reverts to the previous level of lesser stress after the screw head passes.

Similarly, bands 36 can be in a non-straight, e.g. curvilinear or angled, configuration when not being moved by a screw head or other interfering element, and can still move with respect to the bone screw as the bone screw is driven past the band.

If desired, some interfering element other than the head of the screw can be used to activate and release the band. For example, an interfering element (not shown) can be designed into the screw below the head, above the head, or otherwise, for the purpose of activating movement and release of the band.

Whatever the positions of the bands, whatever the interfering element on the screw, which interfaces with the band, once the band is released from the movement caused by the respective interfering element, and the band thus returns to the unmoved location, the band is positioned above, over, and in an interfering and blocking abutment path with some portion of the screw during attempted withdrawal of the screw from the bone support assembly. Referring to FIG. 9B wherein the head of the screw has passed below the bottom of the band, and wherein the band has thus returned to the unmoved position, the band is seen to overlie a portion of the surface of the head of the screw, such that if the screw begins to withdraw e.g. upwardly from the plate, the head of the screw impacts the bottom of the band. When the screw impacts the bottom of the band, the band, being supported by overhanging top walls 34, prevents the screw from further withdrawal from the plate.

As seen in FIG. 9A, when the screw is driven through the plate, e.g. and into bone material of a recipient of such bone support assembly, the force applied by the upwardly-extending angular bottom surface of the screw automatically pushes the band aside as the head of the screw pushes against and passes the band. Once the head of the screw passes the band, the band is automatically restored to the unmoved position over the head of the screw, illustrated in FIG. 9B. Thus, in bone support assemblies of the invention, driving the bone screw, and thereby mounting the bone support assembly in the body of a recipient thereof, automatically moves, optionally flexes, the band, as a locking member, out of the way of insertion of the bone screw, and then the locking member/band automatically moves to a blocking, locking position over the head or other break structure of the screw, thereby automatically activating the blocking and locking feature of the bone support assembly to block withdrawal of the bone screw, and thus to lock the bone screw in the assembly and retain joinder of the bone screw to the respective bone of the recipient. Such bone screw can, of course be released for removal by manually or otherwise intentionally moving or flexing the band and removing the screw while the band is thus held in the moved or flexed condition.

Figure 2:
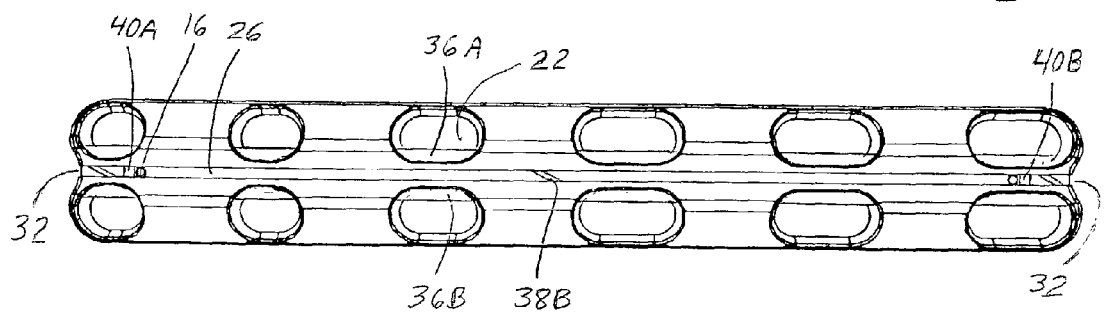
FIG. 2 shows a top view of the bone support assembly illustrated in FIG. 1.
Figure 4:
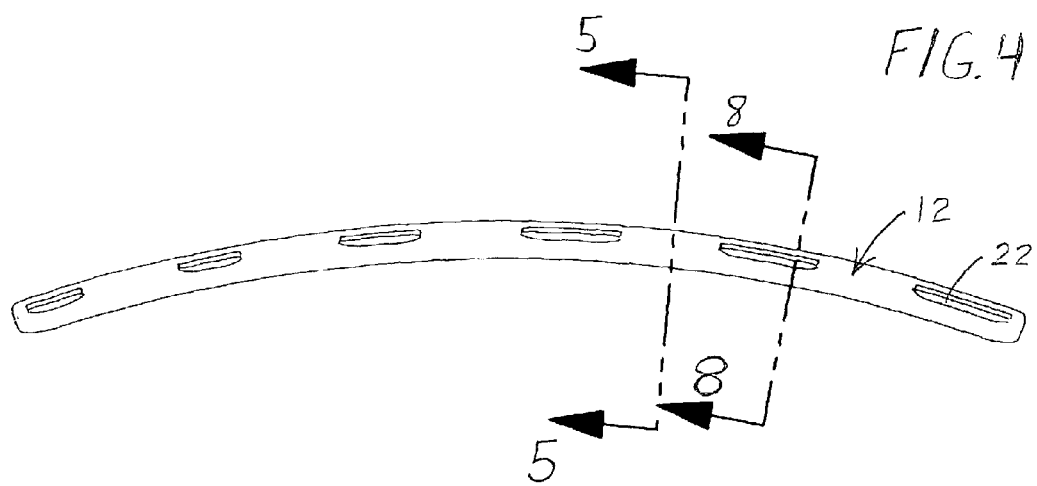
FIG. 4 shows a side view of the bone support assembly illustrated in FIG. 1.
Figure 3:
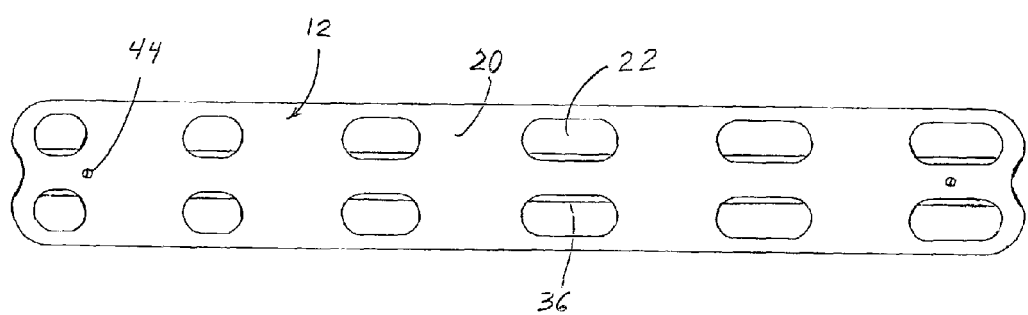
FIG. 3 shows a bottom view of the bone support assembly illustrated in FIG. 1.

In preferred embodiments of the invention, all of apertures 22 are slot-shaped in that each aperture has an elongate dimension and a shorter cross-dimension. Preferably, two of the apertures are relatively lesser lengths, preferably circular, and serve as the support apertures, and the remaining apertures are relatively greater lengths, as slots or slot-shaped, and serve as settle apertures, providing for the bone to settle while being advantageously held by the bone support plate. As seen in FIGS. 1 and 2, typically each aperture along the length of the bone support assembly is progressively longer/shorter than the adjacent apertures in the same row. Typical length increments for adjacent apertures are about 1 mm. Accordingly, in a plate 12 as in FIGS.

1–4 having 6 apertures per row, the length differential between the longest and shortest apertures 22 can be, for example, about 5 mm. The exact and actual length differentials can be somewhat different, depending on the specific use contemplated for the respective plate 12.

Figure 12:
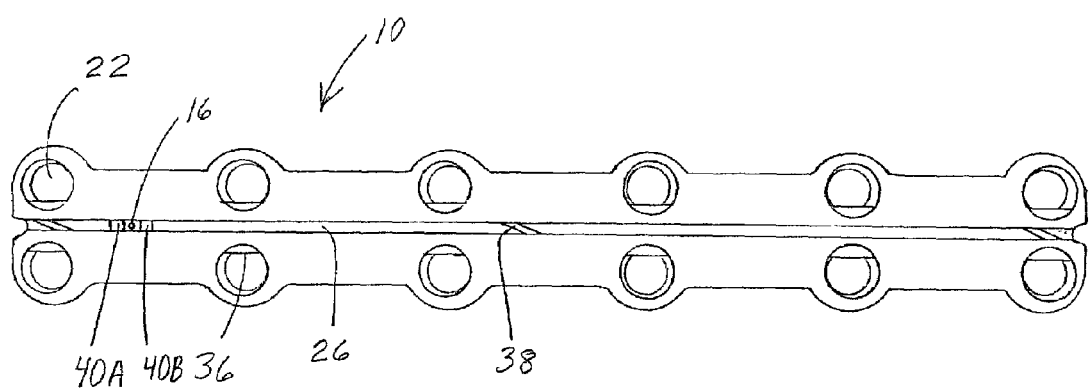
FIG. 12 shows a top view of a second family of embodiments of bone support assemblies as in FIGS. 1–4, and wherein all the bone-fastener-receiving apertures have substantially circular projected open areas.

FIG. 12 illustrates a bone support assembly 10 of the invention wherein all the bone screw apertures 22 are circular. Accordingly, the assembly of FIG. 12 provides for fixed positioning of the bone being supported. Otherwise, all features of the bone support assembly of FIG. 12 are substantially the same as the elements and features of the assemblies of e.g. FIGS. 1–4. Thus, bands 36, springs 38, and studs 16 all employ the same principles illustrated hereinabove.

Typically, bone support assemblies of the invention have two rows of apertures 22. And while the bone support assemblies illustrated in the drawings show 2 rows of bone screw apertures, the invention can well be utilized with any desired number of rows of apertures, and any desired number of apertures per row.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A bone support assembly, comprising:
   (a) a bone support plate, said bone support plate comprising a top surface, a bottom surface opposite the top surface and adapted to engage bone structure of a recipient, first and second ends, and a plurality of bone-fastener-receiving apertures extending between the top surface and the bottom surface for receiving bone fasteners therethrough for securing said bone support assembly to such bone structure of such recipient, said bone support plate further comprising a length and a width, and a thickness between the top surface and the bottom surface, channel structure extending downwardly from the top surface and extending alongside respective ones of the apertures, said channel structure comprising at least one channel having a length, a bottom, and first and second sides, at least one of the first and second sides of the at least one channel having an opening therein extending into a respective said aperture; and
   (b) locking structure in respective ones of said at least one channel, said locking structure in a given said channel having a length, and comprising first and second elongate bands having respective lengths thereof, and extending along the length of the respective said channel, and at least one resilient spring extending between, and connecting, the first and second elongate bands, and urging the first and second bands into engagement with the first and second sides of the respective channel,
   at least one of said first and second bands extending through the opening in the respective side of the channel, and thus extending into the respective aperture, said band being effective, automatically and as a consequence of driving a bone fastener through the respective aperture, to respond to a side force applied by an interfering element of such bone fastener by resiliently moving transversely of the length of the respective said band, and away from such interfering element, and by resiliently returning to a blocking position over the interfering element after such interfering element passes said band.

2. A bone support assembly as in claim 1, said first and second bands comprising resiliently flexible bands, lengths of said bands extending alongside corresponding ones of the apertures whereby, as a such bone fastener is driven, such interfering element of such bone fastener urges said band to automatically flex transversely of the length of said band, from a first flexural condition, until such interfering element in such bone fastener is driven past said band, whereupon said band resiliently returns substantially to the previous flexural condition and overlies such interfering element of the so-driven bone fastener and thereby prevents the bone fastener from withdrawing such interfering element past the band.

3. A bone support assembly as in claim 1, said at least one channel extending along the length of said bone support plate past at least a first row of the apertures and opening into each of the bone-fastener-receiving apertures in the respective row.

4. A bone support assembly as in claim 1 wherein all of said bone-fastener-receiving apertures comprise circular projected openings, and thus have substantially equal projected lengths and projected widths.

5. A bone support assembly as in claim 1 wherein at least all except two of said bone-fastener-receiving apertures have greater lengths, along the length of said bone support plate, than widths transverse to the length of the bone support plate, and thereby comprise slots, enabling longitudinal movement of bone fasteners in said slots, with respect to said bone support plate, thereby to accommodate settling of respective bones to which and adjacent which said bone support assembly is affixed.

6. A bone support assembly as in claim 5 wherein all of said bone-fastener-receiving apertures comprise slots, having lengths greater than respective widths of the respective slots.

7. A bone support assembly as in claim 1, further comprising first and second rows of said bone-fastener-receiving apertures extending along the length of said bone support plate, said at least one channel comprising a said channel extending along the length of said bone support plate, sides of said channel opening into each aperture in the first and second rows of apertures, said first and second elongate bands being urged against the respective first and second sides of the channel, said first elongate band extending into and across portions of respective apertures in the first row, said second elongate band extending into and across portions of respective apertures in the second row.

8. A bone support assembly as in claim 7 wherein said at least one resilient spring comprises at least two compression springs extending between said first and second bands.

9. A bone support assembly as in claim 8 wherein said first and second bands, in combination with said springs, define a unitary structure derived from a single unitary work piece.

10. A bone support assembly as in claim 9 wherein the compositions of said first and second bands comprise predominantly nickel and titanium.

11. A bone support assembly as in claim 9 wherein the compositions of said first and second bands comprise shape memory metal alloys comprising predominantly nickel and titanium, whereby said first and second bands are resiliently flexible bands.

12. A bone support assembly as in claim 7 wherein said first and second bands extend along substantially full lengths of respective first and second sides of the channel, said first and second bands collectively extending into and across portions of each of the bone-fastener-receiving apertures.

13. A bone support assembly as in claim 7 wherein the compositions of said bands are selected from the group consisting of titanium and stainless steel.

14. A bone support assembly as in claim 1, further comprising first and second rows of said bone-fastener-receiving apertures extending along the length of said bone support plate, said at least one channel comprising a said channel extending along the length of said bone support plate, and first and second overhanging top walls of said channel extending inwardly from said sides of said channel and spaced from each other, thereby leaving an opening in the top of the channel between the overhanging top walls and extending along the length of the channel, said overhanging top walls being effective as retainers to restrain movement of said locking structure out of said channel through the top of said channel.

15. A bone support assembly as in claim 14, further comprising first and second band retainers extending from at least one of said first and second bands, each said band retainer on a respective said band extending inwardly toward the other said band, and at least one stud extending into said channel and interacting with said band retainers so as to prevent substantial longitudinal movement of said locking structure along the length of said channel.

16. A bone support assembly as in claim 15, said first and second elongate bands being urged, by said at least one resilient spring, against the respective first and second sides of the channel, and thus into and across a portion of each respective aperture in the first and second rows.

17. A bone support assembly as in claim 16 wherein the compositions of said bands are selected from the group consisting of titanium and stainless steel.

18. A bone support assembly as in claim 15, said first and second band retainers being substantially spaced longitudinally from each other along the length of said locking structure, and interacting with first and second respective said studs spaced from each other, the studs being disposed adjacent respective ones of said retainers so as to prevent substantial movement of said locking structure along the length of said channel.

19. A bone support assembly as in claim 15, said first and second band retainers being closely spaced longitudinally with respect to each other, and interacting with a common said stud, on opposing sides of said stud, so as to prevent substantial movement of said locking structure along the length of said channel.

20. A bone support assembly as in claim 14, said first and second elongate bands being urged, by said at least one resilient spring, against the respective first and second sides of the channel, and thus into and across a portion of each respective aperture in the first and second rows.

21. A bone support assembly as in claim 1, said first and second bands comprising relatively non-resilient bands, the lengths of said bands extending alongside corresponding ones of the apertures whereby, as a such bone fastener is driven, a break structure of such bone fastener urges said band to automatically move from a first position transversely of the length of said band, with corresponding flexing of said at least one resilient spring, from a first flexural condition, until such break structure in such bone fastener is driven past said band, whereupon said spring resiliently returns said band to substantially the first position, and overlies the break structure of the so-driven bone fastener and thereby prevents the bone fastener from withdrawing the break structure past said band.

22. A bone support assembly as in claim 1 wherein said at least one spring comprises at least two springs extending as compressible folded leaves between said first and second bands.

23. A bone support assembly as in claim 22 wherein said first and second bands, and said at least one spring, define a unitary structure derived from a single unitary work piece.

24. A bone support assembly as in claim 1 wherein said first and second bands, and said at least one spring, define a unitary structure derived from a single unitary work piece.

25. A bone support assembly as in claim 1 wherein the compositions of said first and second bands comprise predominantly nickel and titanium.

26. A bone support assembly as in claim 1 wherein the compositions of said first and second bands comprise about 55 percent by weight to about 56 percent by weight nickel and about 44 percent by weight to about 45 percent by weight titanium.

27. A bone support assembly as in claim 1 wherein the compositions of said first and second bands comprise shape memory metal alloys comprising predominantly nickel and titanium, whereby said first and second bands are resiliently flexible bands.

28. A bone support assembly as in claim 1 wherein the compositions of said bands are selected from the group consisting of titanium and stainless steel.

29. A bone support assembly as in claim 1 wherein the compositions of said bands are not shape memory metal alloys, and wherein said bands are sufficiently small in cross-section, and are properly positioned over said apertures, so as to let such bone fastener pass below a respective said band, with transverse movement of said band, and without exceeding a flexural limit of said at least one spring, such that said spring then returns said band to a blocking position over such bone fastener.

30. A bone support assembly as in claim 1 wherein said at least one resilient spring comprises a substantially straight line compression spring integral with said first and second bands, and wherein said spring, in combination with said first and second bands, defines a unitary structure derived from a unitary work piece.

31. A bone support assembly as in claim 30, said at least one spring comprising at least three substantially straight line compression springs.

32. A bone support assembly as in claim 1, said bone-fastener-receiving apertures comprising pairs of said apertures spaced along the length of said bone support plate, said channel structure comprising an elongate channel extending along the length of said bone support plate, said locking structure comprising a plurality of band structures positioned in said channel, disposed lengthwise of each other, and disposed alongside the respective pairs of apertures, spacers being positioned between respective adjacent band structures so as to inhibit substantial longitudinal movement of said band structures.

33. A bone support assembly as in claim 32, said spacers being held in position in said channel by studs extending through said bone support plate and into the channel, and into cooperating apertures in the respective spacers.

34. A bone support assembly as in claim 1, said channel having an opening on at least one of the first and second ends of said bone support plate.

35. A bone support assembly as in claim 34, the opening being adapted and configured to receive said locking structure into said channel by longitudinal movement of said locking structure with respect to said plate.

36. A bone support assembly as in claim 35 wherein all of said bone-fastener-receiving apertures comprise circular projected openings, and thus have substantially equal projected lengths and projected widths.

37. A method of fabricating a bone support assembly, comprising:
   (a) providing a bone support plate having a top surface, a bottom surface opposite the top surface and adapted to engage bone structure of a recipient, and a plurality of bone-fastener-receiving apertures extending between the top surface and the bottom surface for receiving bone fasteners therethrough for securing the bone support assembly to such bone structure of such recipient, the bone support plate further comprising a length and a width, and a thickness between the top surface and the bottom surface, and a channel extending along the length of the bone support plate, the channel having a length, a bottom, a top, and first and second sides, the sides of the channel having openings therein extending into respective ones of the bone-fastener-receiving apertures, the channel having an opening on at least one end of the bone support plate; and
   (b) inserting longitudinally into the channel, through the end opening, a locking structure, the locking structure having a length and comprising first and second bands connected to each other by a plurality of spaced resiliently compressible springs urging the first and second bands into engagement with the first and second sides of the channel when the locking structure is in the channel, whereby the first and second bands extend into, and across, portions of the bone-fastener-receiving apertures; and
   (c) extending one or more locking studs through structure of the bone support plate and into the channel transverse to the length of the locking structure and engaging the locking structure so as to inhibit substantial movement of the locking structure along the length of the channel.

38. A method as in claim 37, the bone support plate defining first and second overhanging top walls of the channel, extending inwardly from the sides of the channel and spaced from each other, the overhanging top walls being effective as retainers to restrain movement of the locking structure out of the channel through the top of the channel.

39. A method of installing a bone support assembly in a recipient thereof, the method comprising:
   (a) providing a bone support assembly comprising
      (i) a bone support plate having a top surface, a bottom surface opposite the top surface and adapted to engage bone structure of a recipient, and a plurality of bone-fastener-receiving apertures extending between the top surface and the bottom surface for receiving bone fasteners therethrough for securing the bone support assembly to such bone structure of such recipient, the bone support plate further comprising a length and a width, and a thickness between the top surface and the bottom surface, and a channel extending along the length of the bone support plate, the channel having a length, a bottom, a top, and first and second sides, the sides of the channel having openings therein extending into respective ones of the bone-fastener-receiving apertures; and
      (ii) a locking structure in the channel, the locking structure having a length and comprising first and second bands connected to each other by a plurality of spaced resiliently compressible springs, urging the first and second bands into engagement with the first and second sides of the channel when the locking structure is in the channel, whereby the first and second bands extend into, and across, portions of the bone-fastener-receiving apertures; and
      (iii) locking studs extending through structure of the bone support plate and into the channel transverse to the length of the locking structure and engaging the locking structure so as to prevent substantial movement of the locking structure along the length of the channel; and
   (b) advancing bone fasteners through selected ones of the bone-fastener-receiving apertures and into bone structure of such recipient, including advancing interfering elements of the bone fasteners past respective ones of the first and second bands, such that a given interfering element causes the respective band to deflect from a first position, transversely of the length of the band as the interfering element passes and such that, when the interfering element moves past the band, the band returns to the first position, thereby occupying a blocking position with respect to the interfering element, thus to automatically inhibit withdrawal of the bone fastener, past the band.

* * * * *